United States Patent
Sano (10) Patent No.: US 10,638,059 B2
(45) Date of Patent: Apr. 28, 2020

(54) RADIATION DETECTION APPARATUS AND RADIATION IMAGING SYSTEM

(71) Applicant: CANON KABUSHIKI KAISHA, Tokyo (JP)

(72) Inventor: Yasuhiko Sano, Sagamihara (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 664 days.

(21) Appl. No.: 15/454,104

(22) Filed: Mar. 9, 2017

(65) Prior Publication Data

US 2017/0269235 A1    Sep. 21, 2017

(30) Foreign Application Priority Data

Mar. 16, 2016  (JP) ................................. 2016-052965

(51) Int. Cl.
| | |
|---|---|
| A61B 6/03 | (2006.01) |
| G01T 1/24 | (2006.01) |
| H01L 27/146 | (2006.01) |
| H04N 5/32 | (2006.01) |
| A61B 6/00 | (2006.01) |
| G01N 23/04 | (2018.01) |

(52) U.S. Cl.
CPC ............. *H04N 5/32* (2013.01); *A61B 6/4233* (2013.01); *G01T 1/247* (2013.01); *H01L 27/14643* (2013.01); *H01L 27/14658* (2013.01); *G01N 23/04* (2013.01)

(58) Field of Classification Search
None
See application file for complete search history.

(56) References Cited

U.S. PATENT DOCUMENTS

| | | | |
|---|---|---|---|
| 6,049,074 A | 4/2000 | Endo et al. | 250/208.1 |
| 9,893,113 B2 * | 2/2018 | Sano | H04N 5/32 |
| 2012/0126126 A1 | 5/2012 | Yokoyama et al. | 250/366 |
| 2016/0178758 A1 | 6/2016 | Sano | G01T 1/17 |

FOREIGN PATENT DOCUMENTS

| | | |
|---|---|---|
| JP | 4018725 | 12/2007 |
| JP | 2012-112726 | 6/2012 |
| JP | 2012-119770 | 6/2012 |

* cited by examiner

*Primary Examiner* — Thomas R Artman
(74) *Attorney, Agent, or Firm* — Venable LLP

(57) ABSTRACT

A radiation detection apparatus comprises a planar radiation detecting panel in which a plurality of detecting units are arranged in a two-dimensional array; an output circuit that drives driving signal lines for driving the detecting units; a readout circuit that reads, via image signal lines, a signal from the detecting units; a conductive layer arranged close to the radiation detecting panel; a first connecting member that connects the ground of the readout circuit and the conductive layer; and a second connecting member that connects the conductive layer and wiring for providing a drive-off bias to the driving signal lines. The first connecting member is connected to the radiation detecting panel in a position between ¼ and ¾ of a length of a side of the radiation detecting panel to which the readout circuit is connected.

18 Claims, 6 Drawing Sheets

RADIATION DETECTION APPARATUS AND RADIATION IMAGING SYSTEM

BACKGROUND OF THE INVENTION

Field of the Invention

The present invention relates to a radiation detection apparatus for detecting radiation, and a radiation imaging system that uses the radiation detection apparatus to capture a radiographic image.

Description of the Related Art

In recent years, a flat panel type radiation detection apparatus that uses a sensor array in which conversion elements for converting radiation to an electrical signal are arranged in a two-dimensional array is spreading. Such a sensor array is commonly configured by making a two-dimensional arrangement of pixels (detecting units), which include a conversion element formed on a glass substrate and a switching element such as TFT for transferring an electrical signal converted by the conversion element to an external unit, into an array. Japanese Patent No. 4018725 (D1) recites a configuration that obtains an image by using such a sensor array. In the configuration recited in D1, a plurality of each of a gate driver for driving a switching element and a sense amplifier for detecting a charge are arranged on the substrate or outside of the glass substrate. The gate drivers drive the switching elements via driving signal lines, the sense amplifier reads electrical signals from the conversion elements via image signal lines, and an image is formed from the read electrical signals.

In an imaging room of a hospital or the like, an apparatus for emitting radiation, another examination apparatus, or the like are installed along with a radiation detection apparatus. There are cases where an apparatus that is used in accordance with a large amount of electric power is included in these apparatuses. In such an environment, electromagnetic energy from an apparatus that uses a large amount of electric power (hereinafter, a high-power apparatus) becomes magnetic field noise for other devices, and may cause a malfunction or a reduction of capabilities in these devices. When an alternating current magnetic field from outside is applied to a radiation detection apparatus for detecting a weak charge, horizontal stripe image noise referred to as line artifacts appear in a captured image. In particular, such noise is generated by a high-power apparatus described above, an inverter of an x-ray generator, or the like, and has a relatively low frequency band of approximately 1 kHz to 100 kHz. In addition, such an alternating current magnetic field may be from various directions due to usage conditions or installation conditions of the radiation detection apparatus and the high-power apparatus.

Japanese Patent Laid-Open No. 2012-119770 (D2) and Japanese Patent Laid-Open No. 2012-112726 (D3) propose configurations for reducing image noise due to an alternating current magnetic field as described above. D2 recites a configuration for adjusting, with respect to an alternating current magnetic field from outside at a specific frequency and a specific amplitude, a read time of a radiographic image and a dark image, and deleting an influence due to the alternating current magnetic field from a final image by subtraction processing. In addition, D3 recites a configuration for reducing an influence of electromagnetic noise by arranging a conductive member, a photoelectric conversion unit, and a scintillator in this order from a side where radiation of the radiation detection apparatus is irradiated.

However, in the technique of D2, if the frequency or the amplitude of the alternating current magnetic field differs between the time of obtaining the dark image and the time of obtaining the radiographic image, it is not possible to remove image noise due to the alternating current magnetic field in the subtraction processing. Furthermore, in D2, setting a time from the start of the obtainment of the dark image until the start of the obtainment of the radiographic image to be an integer multiple of the period of the external magnetic field is required. Therefore, there is the problem that it is necessary to delay the image obtainment interval to align with the period of the external magnetic field, and imaging speed decreases. In addition, there is the necessity to know the period of the external magnetic field in advance. In addition, in D3, while a reduction in relation to electromagnetic noise from a radiation incidence direction is possible, there is the problem that it is difficult to obtain an effect regarding an alternating current magnetic field from a direction horizontal to the radiation detection apparatus.

SUMMARY OF THE INVENTION

By virtue of an embodiment of the present invention, it is possible to reduce image noise due to an alternating current magnetic field in a radiation detection apparatus.

According to one aspect of the present invention, there is provided a radiation detection apparatus, comprising: a planar radiation detecting panel in which a plurality of detecting units for detecting radiation are arranged in a two-dimensional array by driving signal lines and image signal lines; an output circuit configured to drive the driving signal lines to cause driving of the detecting units; a readout circuit configured to read, via the image signal lines, a signal from the detecting units that are driven; a conductive layer arranged close to the radiation detecting panel; a first connecting member that connects the ground of the readout circuit and the conductive layer; and a second connecting member that connects the conductive layer and wiring for providing a drive-off bias to the driving signal lines, wherein a closed circuit in which an induced current caused by an alternating current magnetic field flows is formed by the first connecting member, the second connecting member, the driving signal line, the image signal line, and the conductive layer, and the first connecting member is connected to the radiation detecting panel in a position between ¼ and ¾ of a length of a side of the radiation detecting panel to which the readout circuit is connected.

According to another aspect of the present invention, there is provided a radiation detection apparatus, comprising: a planar radiation detecting panel in which a plurality of detecting units for detecting radiation are arranged in a two-dimensional array by driving signal lines and image signal lines; an output circuit configured to drive the driving signal lines to cause driving of the detecting units; a readout circuit configured to read, via the image signal lines, a signal from the detecting units that are driven; a conductive layer arranged close to the radiation detecting panel; a first connecting member that connects the ground of the readout circuit and the conductive layer; and a second connecting member that connects the conductive layer and wiring for providing a drive-off bias to the driving signal lines, wherein a closed circuit in which an induced current caused by an alternating current magnetic field flows is formed by the first connecting member, the second connecting member, the driving signal line, the image signal line, and the conductive layer, and the second connecting member is connected to the radiation detecting panel in a position between ¼ and ¾ of a length of a side of the radiation detecting panel to which the output circuit is connected.

According to another aspect of the present invention, there is provided a radiation imaging system, comprising: an emitting unit configured to emit radiation; a radiation detection apparatus; and a formation unit configured to irradiate radiation by the emitting unit and form a radiation captured image based on a signal read by the readout circuit of the radiation detection apparatus, wherein the radiation detection apparatus comprises a planar radiation detecting panel in which a plurality of detecting units for detecting radiation are arranged in a two-dimensional array by driving signal lines and image signal lines, an output circuit configured to drive the driving signal lines to cause driving of the detecting units, a readout circuit configured to read, via the image signal lines, a signal from the detecting units that are driven, a conductive layer arranged close to the radiation detecting panel, a first connecting member that connects the ground of the readout circuit and the conductive layer, and a second connecting member that connects the conductive layer and wiring for providing a drive-off bias to the driving signal lines, wherein a closed circuit in which an induced current caused by an alternating current magnetic field flows is formed by the first connecting member, the second connecting member, the driving signal line, the image signal line, and the conductive layer, and the first connecting member is connected to the radiation detecting panel in a position between ¼ and ¾ of a length of a side of the radiation detecting panel to which the readout circuit is connected.

Further features of the present invention will become apparent from the following description of exemplary embodiments (with reference to the attached drawings).

DESCRIPTION OF THE EMBODIMENTS

Explanation is given below, while referring to the attached drawings, regarding an operation principle and a detailed configuration for a radiation detection apparatus according to embodiments of the present invention. The radiation detection apparatus of the embodiments configures a radiation imaging system together with a radiation source for emitting radiation, for example. In such a radiation imaging system, the radiation detection apparatus detects radiation that is emitted from the radiation source, obtains an electrical signal corresponding to a detection result thereof, and forms a radiation captured image. Note that configuration may be taken such that the radiation imaging system is one apparatus that includes all functions for forming a radiation captured image and the radiation source described above, or at the least a portion thereof may exist independently as a separate apparatus. The radiation may be X-rays or may be other radiation.

First Embodiment

Figure 1A:
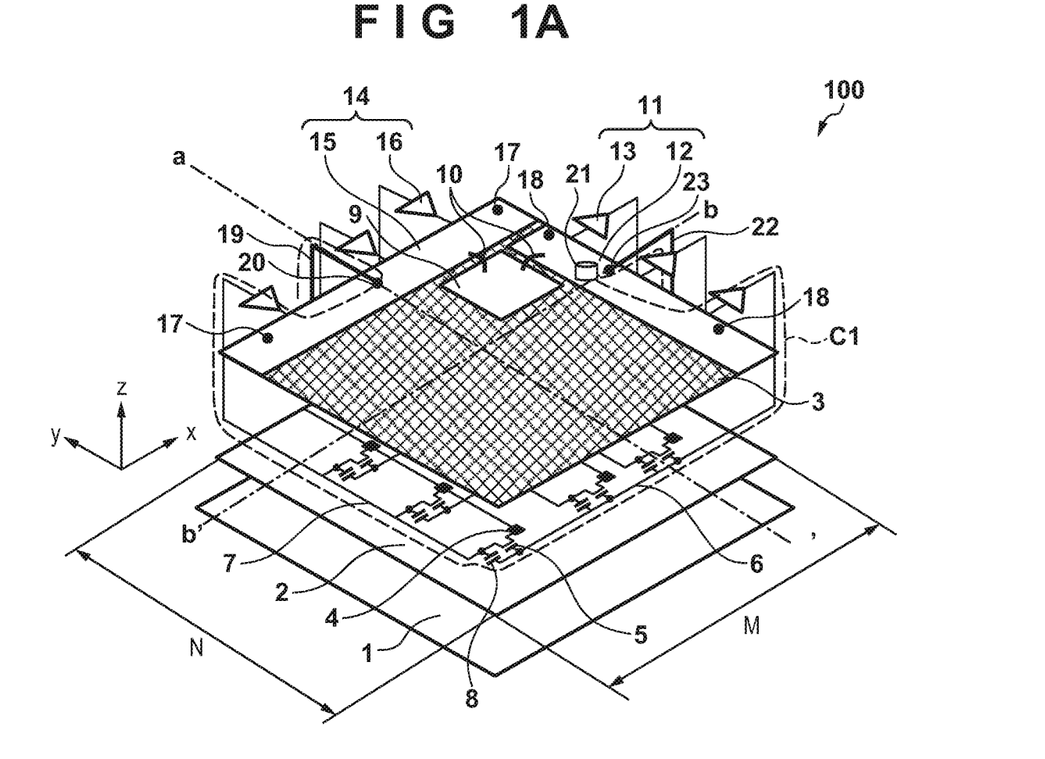
FIGS. 1A and 1B are views that illustrate an example of a structure of a radiation detection apparatus according to a first embodiment.
Figure 1B:
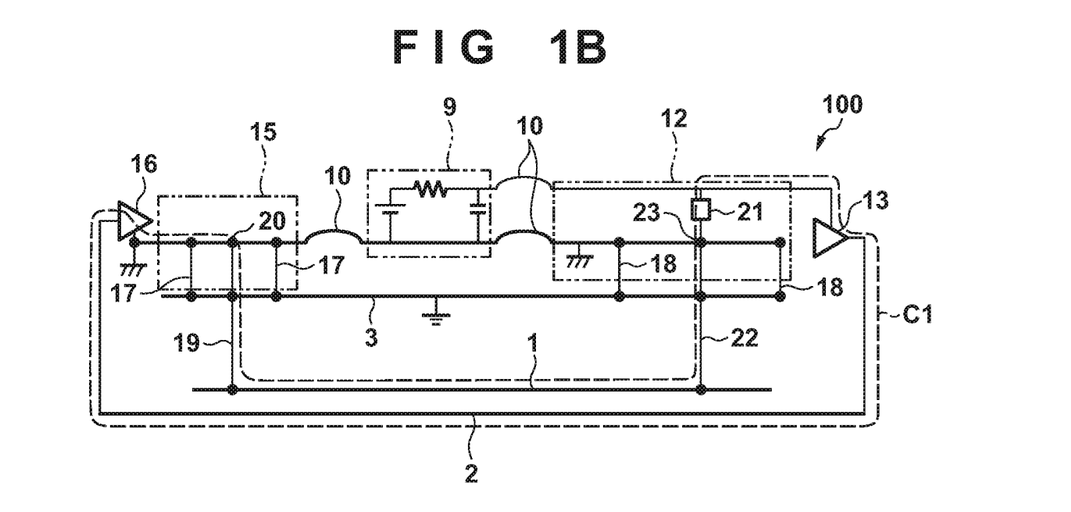

FIG. 1A and FIG. 1B illustrate a structure of a radiation detection apparatus 100 according to this embodiment. FIG. 1A is a perspective view of the radiation detection apparatus 100, and FIG. 1B is a schematic diagram of the circuit of the radiation detection apparatus 100 illustrated in FIG. 1A. Note that, in FIG. 1A, the X axis (X direction), Y axis (Y direction) and Z axis (Z direction) of three-dimensional coordinates are each defined as in the figure. The radiation is assumed to be irradiated from a lower side in the drawing, in other words from a Z axis origin point side. In addition, regarding an alternating current magnetic field that is a source of noise, one from the Z direction is referred to as a vertical direction alternating current magnetic field, and one from an X or a Y direction is referred to as a horizontal direction alternating current magnetic field. The radiation detection apparatus 100 has a configuration in which a conductive layer 1, a sensor array 2, and a support base 3 are overlaid in a direction in which radiation is emitted (in other words the Z direction).

The conductive layer 1 is arranged close to the sensor array 2, and is a sheet type conductive material having an area approximately the same as that of the sensor array 2, or is a conductive thin film that covers the sensor array 2. In FIG. 1A, the conductive layer 1 is arranged more on a radiation irradiation side than the sensor array 2, and is used with the purpose of at least one of preventing detection of visible light that is not radiation, protecting a phosphor (not shown), electric field noise counter-measures, or the like. In such a case, because the conductive layer 1 needs to transmit radiation at a time of capturing, there is a need for it to be a thickness such that radiation transmittance is 99% or more, for example. The conductive layer 1 may be a thin film that includes aluminum of a thickness of approximately 0.1 to 100 μm, for example, that is formed to cover the sensor array 2.

Note that, the conductive layer 1 is not limited to the above, and thus may be formed by another material or have a thickness outside of the above scope if it is a conductive material for which radiation transmittance is 99% or more. In addition, a plurality of conductive layers may be arranged in the Z direction, and in such a case it is advantageous for a conductive layer closest to the sensor array 2 be used as the conductive layer 1 of the present embodiment. In addition, it may be disposed at a position further from the radiation irradiation side than the sensor array 2 if it is the conductive layer closest to the sensor array 2. For example, in a case where a nonconductive support base 3 is used, a conductive layer provided as a frame ground can be adopted as the conductive layer 1 of the present embodiment. In such a case, the conductive layer 1 does not need to transmit radiation at a time of capturing.

Note that the schematic diagram of FIG. 1B differs from FIG. 1A, and illustration is such that the conductive layer 1 is arranged at a position further from the radiation irradiation side than the sensor array 2. This is to facilitate understanding of a closed circuit C1 that is described later, and a similar explanation to that described later holds true even if the conductive layer 1 is more on the radiation irradiation side than the sensor array 2. In addition, the support base 3 is in contact (is connected to the frame ground).

The sensor array 2 is a planar radiation detecting panel in which a plurality of detecting units (pixels) for detecting radiation are arranged in a two-dimensional array by driving signal lines 6 and image signal lines 7 on a substrate having an insulating surface such as glass. Each of the plurality of detecting units includes a conversion element 4 and a switching element 5. In addition, the driving signal lines 6 which are for driving the switching element 5 and the image signal lines 7 which are for causing a radiation detection result by a conversion element 4 to be output via the switching element 5 are wired to the sensor array 2. Note that, in the sensor array 2, a parasitic capacitance 8 may be present as an unintended static capacitance formed due to the structure of the switching element 5 or intersection of a driving signal line 6 and an image signal line 7.

The conversion elements 4 is an element for converting radiation (or light generated by a scintillator (not shown)) into an electrical signal. The switching elements 5 are configured by a thin film transistor (TFT) or the like, for example. As described above, a conversion element 4 and a switching element 5 as a pair configure a detecting unit that corresponds to one pixel, and the detecting units are arranged in a two-dimensional array in the sensor array 2, and function as a radiation detecting panel for obtaining a radiation captured image composed from a plurality of pixels. A driving signal line 6 is arranged in correspondence with each line in the two-dimensional array of the detecting unit, and supplies either of a drive-on bias and a drive-off bias to the switching element 5 of the detecting units of each row. The drive-on bias and the drive-off bias are supplied to the driving signal line 6 by a power supply board 9 from an output unit 11, and via a flexible board 10. However, there is no limitation to this configuration, and the drive-on bias and the drive-off bias may be supplied by, for example, a readout board 15 explained later, or a power supply IC provided on an output board 12.

Each output unit 11 is configured from the output board 12 and an output circuit 13, and functions as a driving circuit for driving each of the above switching elements 5. The output circuit 13 drives the driving signal line 6 which is for causing driving of a detecting unit. In other words, the output circuit 13 selectively applies to the driving signal line 6 either of a drive-on bias for setting the switching element 5 to on, or a drive-off bias for setting it to off. The drive-on bias, the drive-off bias, and a digital signal for controlling operation of the output circuit 13 is input to the output circuit 13. The output board 12 performs input and output of the control signal to the output circuit 13, and supplies power to the output circuit 13. Note that it is sufficient if the drive-off bias is a potential that can set the switching element 5 to an off state and, in the present embodiment, the drive-off bias is a potential that is supplied by the power supply board 9 via the flexible board 10, for example. In addition, in a variation (FIG. 5) described later, the drive-off bias is a ground potential.

The image signal line 7 is arranged for each row of the two-dimensional array of the detecting units. An electrical signal, in other words a radiation detection result of the conversion element 4 corresponding to the switching element 5 to which the drive-on bias is supplied by the driving signal line 6 is transmitted to a readout unit 14. Each readout unit 14 is configured from the readout board 15 and a readout circuit 16, and functions as an obtainment circuit for obtaining a radiation detection result. The readout circuit 16 reads a signal from a driven detecting unit via the image signal line 7. The readout circuit 16 converts an electrical signal from the image signal line 7 into a digital signal by an A/D converter or the like, and transmits it to the readout board 15. The readout board 15, for example, performs input and output of control signals with respect to the readout circuit 16, and may also supply power depending on the situation.

The readout board 15 and the output board 12 are each arranged and fixed on the support base 3 by a plurality of first fixing portions 17 and a plurality of second fixing portions 18, using fixing members such as screws. The support base 3 is a base for fixing and supporting the sensor array 2, the readout board 15, and the output board 12. The support base 3 is formed by a conductive metal, or, in response to desires for weight saving in recent years, something that sandwiches a metal mesh by carbon fiber reinforced plastic (CFRP) which is lightweight and has high strength, CFRP on its own, or the like. If the support base 3 is a nonconductive material such as CFRP on its own, it is formed by sandwiching a conductive layer between the support base 3 and the sensor array 2 to cause the support base 3 to function as the frame ground. In addition, a conductive member that functions as the frame ground may be arranged between the support base 3 and the sensor array 2. This conductive member can also be used as the conductive layer 1 described above. Note that the readout board 15 and the output board 12 are fixed to a surface of the support base 3 opposite the surface to which the sensor array 2 is fixed.

Each of the output circuits 13 and the readout circuits 16 are commonly configured by an integrated circuit, and are mounted on a flexible board such as TCP (Tape Carrier Package), COF (Chip On Film), or the like (not shown). In addition, the output circuits 13 and the readout circuits 16 may be mounted on the sensor array 2 by a mounting method referred to as COG (Chip On Glass) for example.

A first connecting member 19 is a member that is connected to the conductive layer 1 and the ground of the readout circuits 16 (the readout board 15). If a length of a side of the sensor array 2 on which the readout circuits 16 are mounted is M, the first connecting member 19 is connected to the ground of the readout board 15 by being connected to a first connection point 20 provided at an approximately central (M/2) position. A first impedance element 21 is provided in the output board 12, and is connected between the drive-off bias and the ground of the output board 12. The first impedance element 21 handles a role of distributing a noise component to the conductive layer 1 as later described, and a capacitor is used for example. As with the formation of the closed circuit C1, which is illustrated in FIG. 1B, in relation to induced electromotive force caused by an alternating current magnetic field, a second connecting member 22 connects the conductive layer 1 with wiring for providing the drive-off bias to the driving signal line. In the present embodiment, the second connecting member 22 is a member for connecting the conductive layer 1 and the ground of the first impedance element 21. In other words, the second connecting member 22 connects the conductive layer 1 with wiring for providing the drive-off bias via the first impedance element 21. If a length of a side of the sensor array 2 on which the output circuits 13 are mounted is N, the second connecting member 22 is connected to the ground of the first impedance element 21 by being connected to a second connection point 23 provided at an approximately central (N/2) position.

Figure 2A:
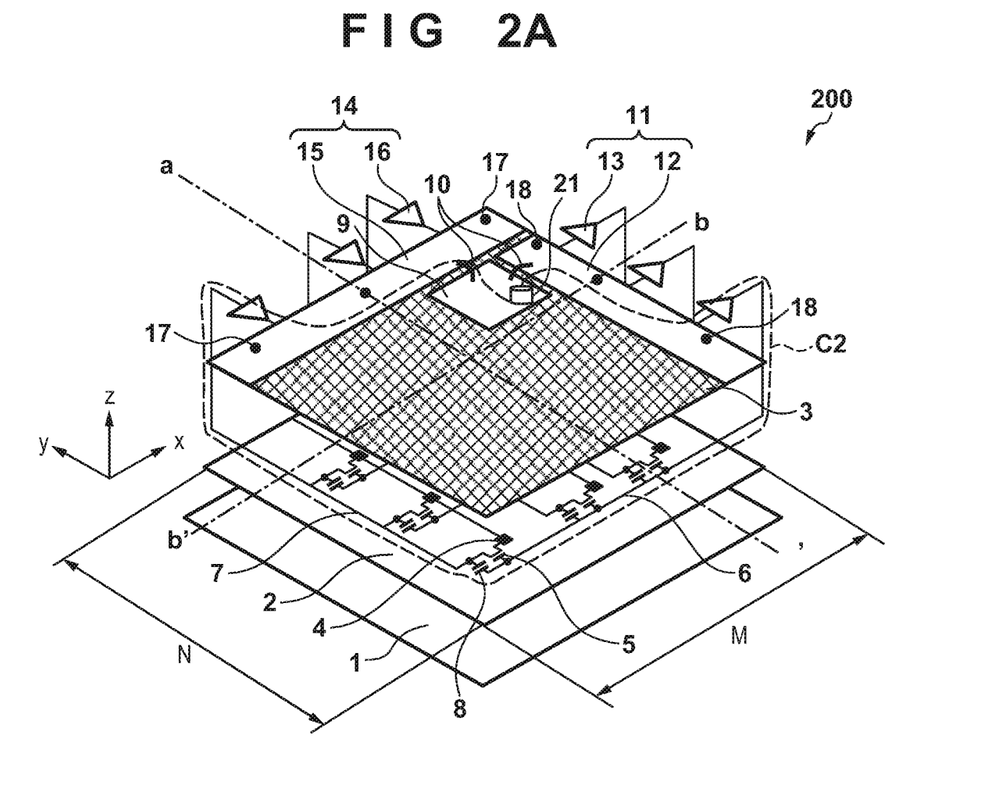
FIGS. 2A and 2B are views that illustrate a structure of a radiation detection apparatus as a comparative example.
Figure 2B:
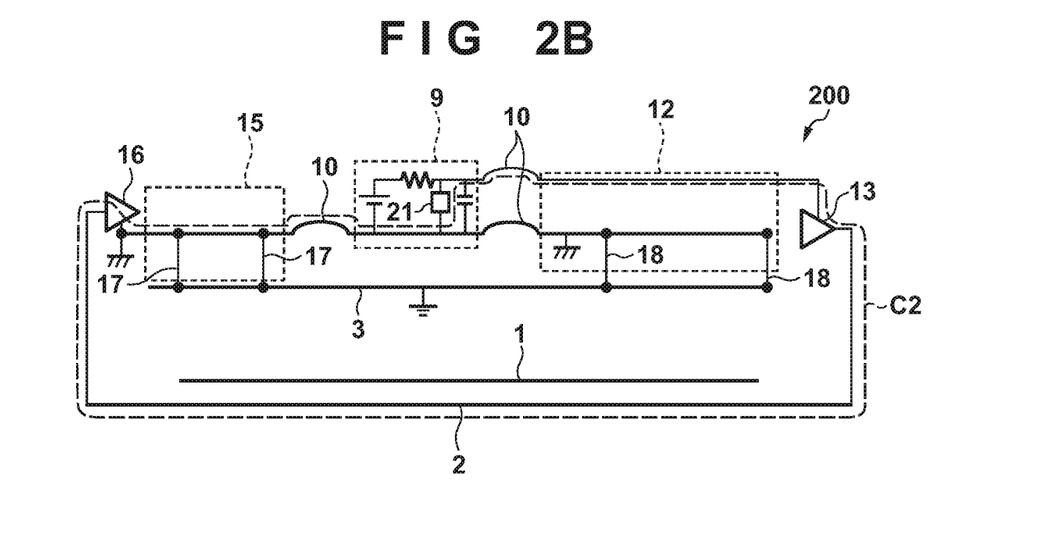

Explanation using a comparative example of FIG. 2A and FIG. 2B is given below regarding an operation principle of the radiation detection apparatus 100 of the present embodiment concerning reduction of noise caused by a magnetic field. FIG. 2A and FIG. 2B are views that illustrate a structure of a radiation detection apparatus 200 as a comparative example. The radiation detection apparatus 200 has a configuration of a typical radiation detection apparatus, in which the first connecting member 19 and the second connecting member 22 are not present, and the first impedance element 21 is mounted on the power supply board 9. FIG. 2A is a perspective view of the radiation detection apparatus 200, and FIG. 2B is a schematic diagram of the circuit of the radiation detection apparatus 200 of FIG. 2A. Note that, in FIG. 2A and FIG. 2B, the same reference numeral is added to the configuration portions that are the same as those of FIG. 1A and FIG. 1B.

In the radiation detection apparatuses 100 and 200, by the principle of electromagnetic induction, an induced electromotive force arises by an alternating current magnetic field, in other words magnetic flux that fluctuates, passing through or in other words intersecting with a closed circuit in the radiation detection apparatus. Image noise is generated by the induced electromotive force being superimposed with the electrical signal detected by the readout circuits 16. It is known that the induced electromotive force is proportional to the cross-sectional area of the closed circuit intersected by the alternating current magnetic field and the magnetic flux density of the alternating current magnetic field.

In FIG. 2A and FIG. 2B, the closed circuit that the alternating current magnetic field intersects is illustrated by C2. The closed circuit C2 is formed by one of the readout circuits 16 to the sensor array 2 to one of the output circuits 13 to (the wiring for supplying the drive-off bias of) the output board 12 to (the wiring for supplying the drive-off bias of) the flexible board 10 to the first impedance element 21 to (the ground of) the flexible board 10 to (the ground of) the readout board 15, and finally reaches the one of the readout circuits 16. Here, on the sensor array 2, an induced electromotive force propagation path from the image signal line 7 to the driving signal line 6 is formed by the parasitic capacitance 8. Note that although one closed circuit C2 is described by FIG. 2A and FIG. 2B, actually a plurality of the closed circuit C2 are formed by all of the driving signal lines 6 with respect to one of the image signal lines 7. Cross-sectional areas or path lengths of the closed circuits are respectively different in accordance with a physical arrangement position of the circuit configurations that form the closed circuits. An image noise amount superimposed on a signal that flows through one of the image signal lines 7 is represented by a sum total of the induced electromotive force vectors induced by all of the closed circuits.

Figure 3A:
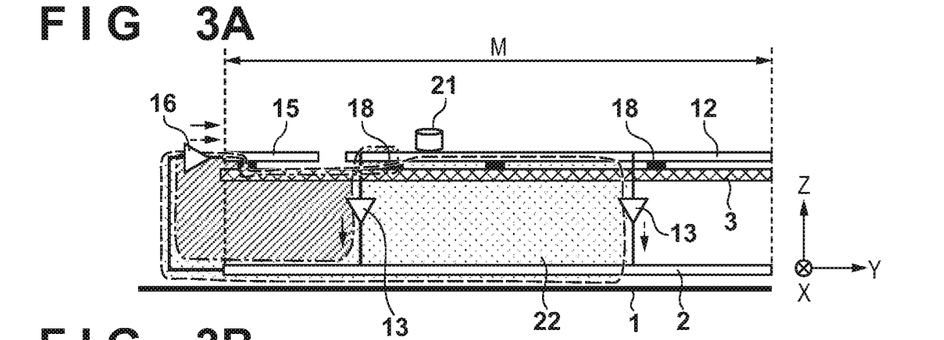
FIGS. 3A to 3D are cross-sectional views illustrating states in which an alternating current magnetic field intersects with a radiation detection apparatus as comparative examples.

Using FIGS. 3A to 3D, explanation is given in detail regarding the above induced electromotive force. FIG. 3A is something that, in the case where FIG. 2A is seen from the cross section a-a', represents a state where two closed circuits are formed in one readout circuit 16 (one of the image signal lines 7). In the drawings, the closed circuits that form regions filled by points or diagonal lines are closed circuits C2 illustrated by FIG. 2A, in other words the closed circuits formed by the readout circuit 16 and the output circuits 13. The filled portions are cross-sectional areas through which an alternating current magnetic field from the X direction (in other words an alternating current magnetic field that is orthogonal to the paper surface) passes. In FIG. 3A, the cross-sectional area through which the alternating current magnetic field passes of the closed circuit formed by the output circuit 13 on the right side and the readout circuit 16 is the region filled by points+the region filled by diagonal lines. In addition, the cross-sectional area through which the alternating current magnetic field passes of the closed circuit formed by the output circuit 13 on the left side and the readout circuit 16 is the region filled by diagonal lines.

Such a closed circuit is present for all of the output circuits 13, and an image noise amount in the readout circuit 16 that corresponds to one image signal line is the vector sum of the induced electromotive force induced by all of these closed circuits. Here consideration is given regarding a direction of the induced electromotive force that is induced in the readout circuit 16. When the induced electromotive force that is induced in the region filled by points is indicated by a dashed line arrow and the induced electromotive force that is induced in the region filled by diagonal lines is indicated by a solid line arrow, it is understood that the induced electromotive force is generated in the same direction with respect to the alternating current magnetic field noise that is from the same direction. Therefore, for the sum total of the induced electromotive force, there is a synergistic effect due to the plurality of closed circuits, and the image noise amount becomes large.

Figure 3B:
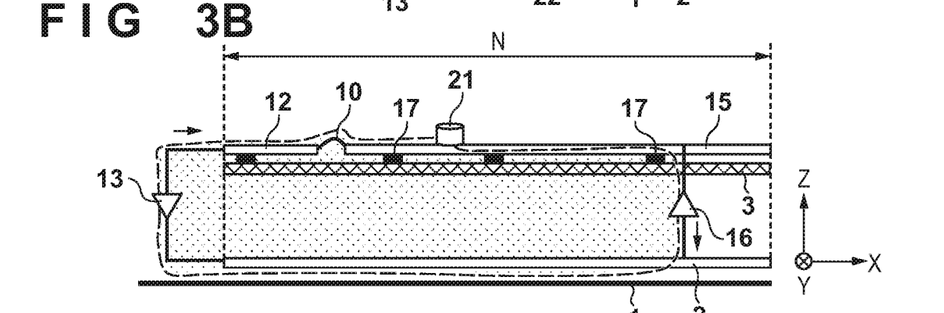
Figure 3C:
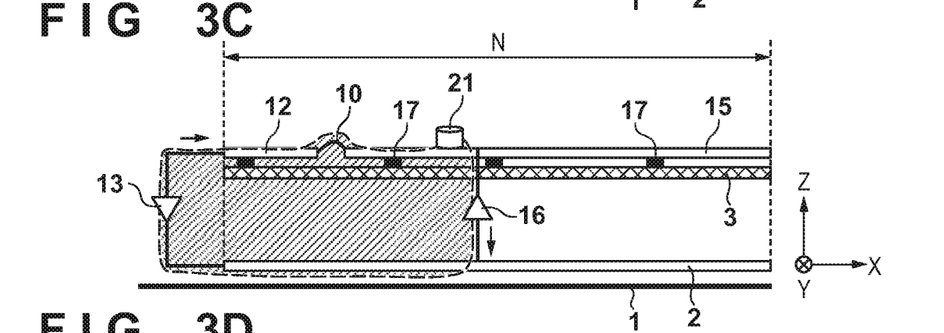

Next, when FIG. 2A is seen from the cross-section b-b', a situation in which the closed circuit C2 is formed for one readout circuit 16 at a position separated from the output board 12 is illustrated in FIG. 3B. Similarly in this case, a region filled by points is the cross-sectional area of a closed circuit through which an alternating current magnetic field passes. Although there is one closed circuit illustrated in the drawing, a plurality of closed circuits formed by the plurality of other output circuits 13 is present in the depth direction. In addition, FIG. 3C illustrates a closed circuit formed by the readout circuit 16 which is arranged at an almost central portion of the sensor array 2, and a region filled by diagonal lines indicates a cross-sectional area through which an alternating current magnetic field passes. Here, when a comparison with the previous region of FIG. 3B is made, it can be seen that the region of FIG. 3C has a cross-sectional area that is smaller in proportion to how much closer the readout circuit 16 is to the output circuit 13.

Figure 3D:
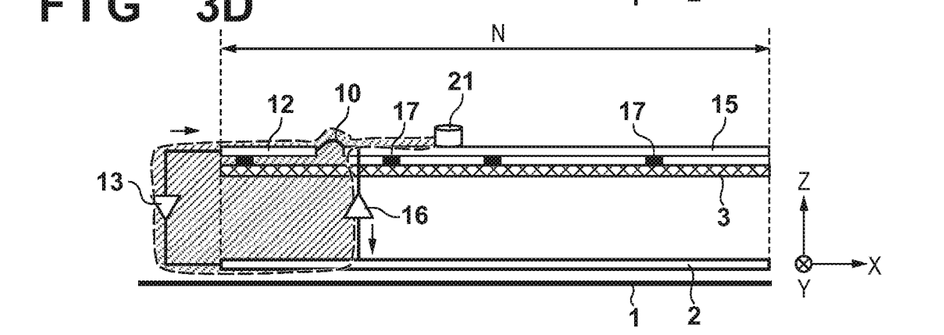

Furthermore, a closed circuit in the case when a readout circuit 16 is close to an output circuit 13 and a cross-sectional area through which an alternating current magnetic field passes is illustrated in FIG. 3D. In comparison to the previous FIG. 3C, it can be seen that the cross-sectional area is even smaller. In other words, in the radiation detection apparatus 200, the image noise of a readout circuit 16 which is arranged farther from an output circuit 13 is larger in relation to the alternating current magnetic field from the Y direction as in FIG. 3B to FIG. 3D. The closer the readout circuit 16 is to an output circuit 13, the smaller the image noise amount is.

In contrast to this, in the radiation detection apparatus 100 illustrated in FIG. 1A and FIG. 1B, the first impedance element 21 is provided on the output board 12, and is connected between the drive-off bias and the ground of the output board 12. Furthermore, the first connecting member 19 that connects the conductive layer 1 and the ground of the readout board 15 is arranged at an approximate center with respect to the length M of the side of the sensor array 2 to which the readout circuits 16 are connected. Furthermore, the second connecting member 22 that connects the conductive layer 1 and the ground of the first impedance element is arranged at an approximate center with respect to the length N of the side of the sensor array 2 to which the output circuits 13 are connected.

In accordance with the above configuration, a closed circuit C1 in which an induced current caused by the alternating current magnetic field flows is formed by the first connecting member 19, the second connecting member 22, the driving signal line 6, the image signal line 7, and the conductive layer 1. More specifically, the closed circuit C1 that is influenced by the alternating current magnetic field noise is formed as illustrated in FIG. 1B. The closed circuit C1 illustrated in FIG. 1B is formed by one of the readout circuits 16 to the sensor array 2 to one of the output circuits 13 to (the wiring for supplying the drive-off bias of) the output board 12 to the first impedance element 21 to the second connecting member 22 to the conductive layer 1 to the first connecting member 19 to (the ground of the readout board 15). Here, on the sensor array 2, a propagation path from the image signal line 7 to the driving signal line 6 is formed by the parasitic capacitance 8. Although one closed circuit C1 is described by FIG. 1A and FIG. 1B, actually a plurality of closed circuits C1 are formed by all of the driving signal lines 6 with respect to one of the image signal lines 7. Cross-sectional areas or path lengths of the plurality of closed circuits differ in accordance with a physical arrangement position of the circuit configurations for forming the closed circuits. An image noise amount with respect to one of the image signal lines 7 is represented by a sum total of the induced electromotive force vectors induced by all of the closed circuits.

Here, it is necessary to set the first impedance element 21 and the second connecting member 22 as a main path of the induced electromotive force, to form the closed circuits C1 in relation to the induced electromotive force that is induced by the external alternating current magnetic field. The main frequency band of the external alternating current magnetic field is 1 kHz to 100 kHz, and because the first impedance element 21 is the main path of the induced electromotive force, it is necessary for the first impedance element 21 to be a sufficiently low impedance in this frequency band. In the case of the present embodiment, if the first impedance element 21 is less than or equal to the impedance of the power supply for supplying the drive-off bias, the first impedance element 21 can be set as a main path, and the closed circuit C1 as illustrated in FIG. 1B can be formed. Note that a capacitor is used as the first impedance element 21 in the present embodiment, but this is no limitation to this, and it may be something like an LC filter for example.

Figure 4A:
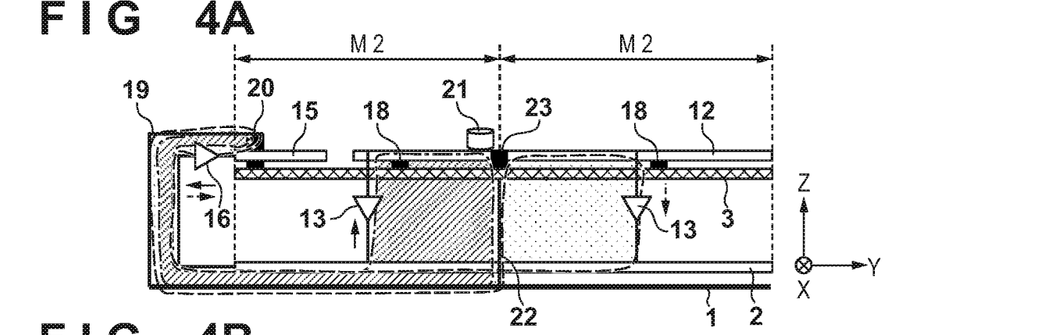
FIGS. 4A to 4D are cross-sectional views illustrating situations in which an alternating current magnetic field intersects in a first example of the radiation detection apparatus.

Using FIGS. 4A through 4D, explanation is given below regarding closed circuits seen from each of the X direction and the Y direction in the radiation detection apparatus 100 of the present embodiment, compared to the case of the radiation detection apparatus 200 (FIGS. 3A to 3D). FIG. 4A is something that represents a state in which two closed circuits are formed with respect to one readout circuit 16 by the second connecting member 22, in a case where the radiation detection apparatus 100 of FIG. 1A is seen from the cross section a-a'. In the drawing, a region filled by points is the closed circuit C1 formed by the output circuit 13 (the output circuit 13 on the right side in the drawing) at a position separated from the readout circuit 16. A filled portion is a cross-sectional area through which an alternating current magnetic field from the X direction, in other words orthogonal to the paper surface, passes.

Meanwhile, the region filled by diagonal lines is a closed circuit formed by the output circuit 13 at a position close to the readout circuit 16, and this closed circuit is also a cross-sectional area that through which an alternating current magnetic field similarly passes. Here consideration is given regarding a direction of the induced electromotive force that is induced in the readout circuit 16. An induced electromotive force that is induced in the region filled by points is illustrated by dashed line arrows, and an induced electromotive force that is induced in the region filled by diagonal lines is illustrated by solid line arrows. Looking at these, the induced electromotive force of the readout circuit 16 is induced in the two closed circuits in directions that cancel each other out. Therefore, the sum total in the readout circuit 16 of the induced electromotive force generated by these two closed circuits becomes significantly smaller. In this way, by the induced electromotive forces of the closed circuit of the side closer to the readout circuit 16 than the second connecting member 22 and the closed circuit of the side further from it being cancelled out, it is possible to significantly reduce image noise (hereinafter, a cancelling effect).

FIG. 4A illustrates a pair of two closed circuits at approximately equal distances from the second connecting member 22, of the side closer to the readout circuit 16 from the second connecting member 22 and the side from further it. By the plurality of the output circuits 13, a plurality of such a pair of closed circuits exist, and thus the induced electromotive forces in the readout circuits 16 is cancelled out, and the sum total of the induced electromotive force decreases. In particular, by arranging the second connecting member 22 at an approximate center of a side on which the output circuits 13 are mounted (a position of approximately N/2), and by pairs as described above being formed for substantially all of the output circuits 13, it is possible to more effectively cause the sum total of the induced electromotive force to decrease.

Figure 4B:
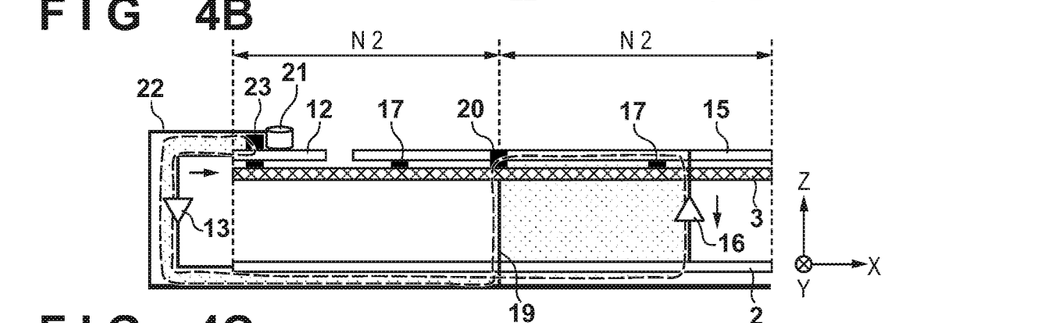

Next, when FIG. 1A is seen from the cross-section b-b', a situation in which the closed circuit C1 is formed for one readout circuit 16 at a position separated from the output board 12 is illustrated in FIG. 4B. In FIG. 4B, a region filled by points is the cross-sectional area of a closed circuit through which an alternating current magnetic field passes in the Y direction. Note that, although there is only one closed circuit illustrated in the drawing, a plurality of closed circuits formed by the plurality of other output circuits 13 is present in the depth direction.

Here, a comparison is made with the closed circuit (FIG. 3B) formed by the output circuit 13 at a similar position in the radiation detection apparatus 200 and its cross-sectional area. In the case of FIG. 3B, because the first connecting member 19 is not present, the path between the output circuit 13 and the readout circuit 16 forms the paths between the readout board 15 and the sensor array 2 which are separated by a distance from each other, and the cross-sectional area through which an alternating current magnetic field passes is larger. In contrast to this, in the case of FIG. 4B, because the propagation path is in the conductive layer 1 which is close to the sensor array 2 at a position of the first connecting member 19, the cross-sectional area through which the alternating current magnetic field passes decreases (hereinafter, an area reduction effect).

Figure 4C:
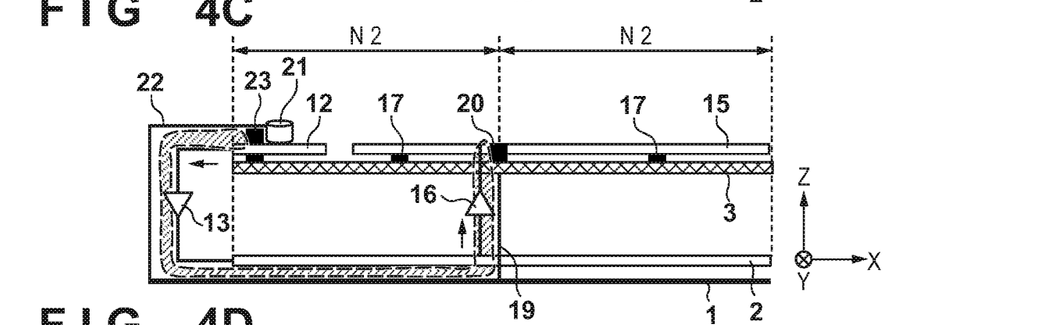
Figure 4D:
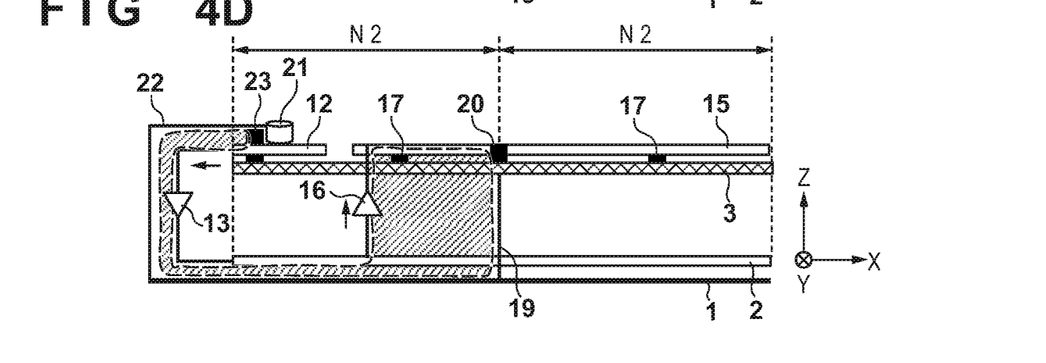

Next, consideration is given to an induced electromotive force that is induced in the readout circuit 16 at a position approximately the same as the first connecting member 19, in FIG. 4C. In such a case, a region filled by diagonal lines is the cross-sectional area of the closed circuit through which the alternating current magnetic field passes, and compared to FIG. 3C, an induced electromotive force of a level that can be substantially ignored results. Accordingly, an image noise amount at the readout circuit 16 that is at a position approximately the same as the first connecting member, in other words approximately central, becomes an amount that can be substantially ignored, and it is possible to make a significant reduction in comparison to what was conventional. Furthermore, examination is made regarding an induced electromotive force that is induced in the readout circuit 16 arranged on a side of the output circuit 13 away from the first connecting member 19, as in FIG. 4D. In this case, a region filled by diagonal lines in FIG. 4D is the cross-sectional area of a closed circuit through which an alternating current magnetic field passes. In such a case it becomes a cross-sectional area approximately equivalent to that of FIG. 3D.

In particular, it is possible to cause the cross-sectional area through which an alternating current magnetic field passes to significantly decrease by connecting the first connecting member 19 to an approximate center of the side of the sensor array 2 at which the output circuits 13 are mounted. For example, in the state of FIG. 4B, the cross-sectional area through which the alternating current magnetic field passes is approximately halved. Because the image noise, in other words the size of the induced electromotive force, is proportional to the cross-sectional area of the closed circuit intersected by an alternating current magnetic field, it is also possible to cause the image noise to significantly decrease.

As described above, when focusing on one of the readout circuits 16, a cancelling effect due to a plurality of closed circuits in accordance with the second connecting member 22 is achieved for the induced electromotive force caused by an alternating current magnetic field of the X direction, and the image noise is reduced. In addition, the induced electromotive force caused by an alternating current magnetic field of the Y direction is reduced by the area reduction effect due to the first connecting member 19, and the image noise is reduced. In particular, it is possible to more effectively cause image noise to decrease by arranging the second connecting member 22 at an approximate center of a side of the sensor array 2 where the output circuits 13 are mounted, and arranging the first connecting member 19 at an approximate center of a side of the sensor array 2 where the readout circuits 16 are mounted.

Note that approximate center is not limited to meaning only a configuration in which it is arranged strictly at the center. For example, approximate center means a configuration in which a state of being arranged at the center substantially is maintained even if there is a certain amount of deviation from the center due to assembly error or the arrangement of the circuit. In addition, there may be cases where the first connecting member 19 or the second connecting member 22 cannot necessarily be arranged at the center due to the circuit arrangement. In such a case, it is possible to obtain the cancelling effect for the X direction when in the range of ¼ to ¾ of the side of the sensor array 2, and for the Y direction a reduction effect for 50% or more of the noise can be obtained in comparison to a case where the first connecting member 19 is not present. Furthermore, in the present embodiment, there was one of each the first connecting member 19 and the second connecting member 22, but there is no limitation to this, and a reduction effect can be obtained even if there is a plurality of these if they are in the range of ¼ to ¾ described above.

As described above, provided in the radiation detection apparatus 100 are the first connecting member 19 that is connected to the conductive layer 1 and the ground of the readout circuits 16, and the second connecting member 22 that is connected to the conductive layer 1 and the wiring for providing the drive-off bias to the driving signal line 6. By virtue of the present embodiment, by the first connecting member 19 and the second connecting member 22, the conductive layer 1 is included in the path of the closed circuit through which an induced current caused by an alternating current magnetic field flows, including the driving signal line 6 and the image signal line 7, as illustrated in FIG. 1B. As a result, by the area reduction effect due to the first connecting member 19 or the cancelling effect due to the second connecting member 22 as explained by FIGS. 4A to 4D, the image noise is reduced.

Figure 5:
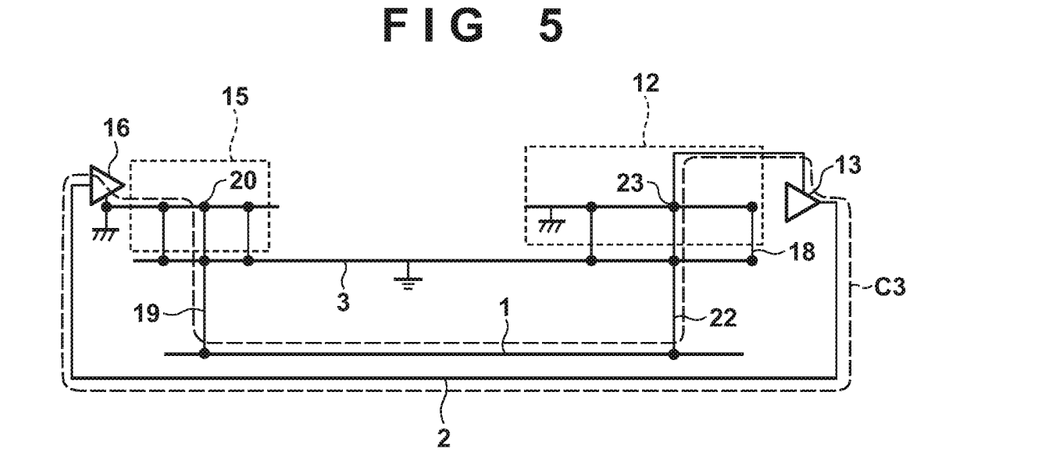
FIG. 5 is a view that illustrates an example of a radiation detection apparatus in a case where a drive-off bias is a ground potential.

Although explanation was given above of a configuration in which the second connecting member 22 connects the wiring for providing the drive-off bias and the conductive layer 1 via the first impedance element 21, configuration may be taken such that the first impedance element 21 is not used if the drive-off bias is the ground potential. In such a case, by short-circuiting between the drive-off bias and the ground of the output board 12 as illustrated in FIG. 5, it is possible to have the second connecting member be the main path for an induced electromotive force due to an alternating current magnetic field. As a result, as explained by FIGS. 4A to 4D, a closed circuit C3 of the induced electromotive force is formed so as to include the conductive layer 1 as a path, and it is possible to obtain a noise reduction effect similar to that of the above embodiment.

Second Embodiment

In the first embodiment, the second connecting member 22 and the ground side of the first impedance element 21 are directly connected to the ground of the output board 12 and the support base 3. However, configuration may be taken such that the second connecting member 22 and the ground side of the first impedance element 21 are not directly connected to the ground of the output board 12 or the support base 3, and they may be connected via a predetermined impedance element. In the second embodiment, explanation is given of a configuration in which the second connecting member 22 and the ground side of the first impedance element 21 are connected to the ground of the output board 12 and the support base 3, respectively via second and third impedance elements.

Figure 6:
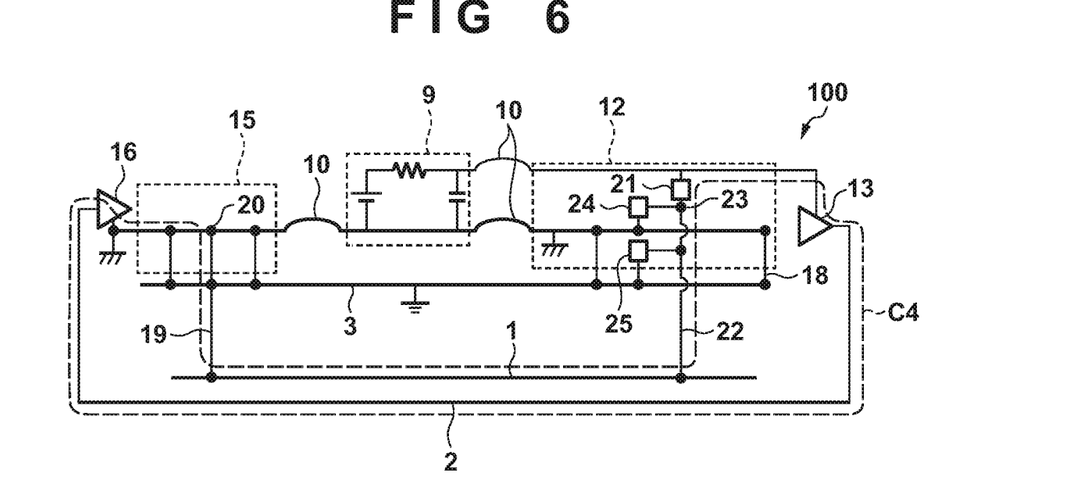
FIG. 6 is a view that illustrates an example of a structure of a radiation detection apparatus according to a second embodiment.

FIG. 6 illustrates a second example of the structure of the radiation detection apparatus 100. In FIG. 6, although only a schematic diagram of a circuit is illustrated, the basic structure is similar to FIG. 1A, and the first impedance element 21, the first connecting member 19, and the second connecting member 22 are arranged at positions that are similar to those in the first embodiment. Note that, in the second embodiment (FIG. 6), the same reference numerals are added for configurations that are the same as the first embodiment (FIG. 1A, FIG. 1B).

In the radiation detection apparatus 100 of the second embodiment, a second impedance element 24 is added between the ground of the output board 12 and a second connection point 23. Furthermore, a third impedance element 25 is added between the support base 3 and the second connecting member 22. A closed circuit C4 through which an alternating current magnetic field passes is similar to the closed circuit C1 in the first embodiment. However, in the first embodiment, because the ground of the first impedance element 21 is short-circuited to connect to the support base 3 and the ground of the output board 12, a portion of the induced electromotive force is diverted to the support base 3 or the ground of the output board 12. In contrast to this, in the second embodiment, by providing the second impedance element 24 and the third impedance element 25 as in FIG. 6, diversion to the ground of the output board 12 and the support base 3 is prevented. By this, it is possible to achieve to a maximum cancellation of the induced electromotive force in relation to an alternating current magnetic field of the X direction and an area reduction effect in relation to an alternating current magnetic field of the Y direction discussed in the first embodiment, and further reduction of image noise becomes possible.

Discussion is given here regarding suitable values of the second impedance element 24 and the third impedance element 25. An induced current that flows/leaks from the ground of the first impedance element 21 to the ground of the readout board 15 diverts to four paths.

(1) The summation of the impedance of the conductive layer 1, the first connecting member 19, and the second connecting member 22.

(2) The summation of the impedance of the ground of the output board 12, the support base 3, and the second impedance element 24.

(3) The summation of the impedance of the ground of the output board 12, the ground of the flexible board 10, the ground of the power supply board 9, and the second impedance element 24.

(4) The summation of the impedance of the support base 3 and the third impedance element 25.

Accordingly, to cause an induced current to efficiently divert to the conductive layer 1, it is sufficient if the second impedance element 24 and the third impedance element 25 are set to greater than or equal to (1) the summation of the impedance of the conductive layer 1, the first connecting member 19, and the second connecting member 22. Here, regarding (1) the summation of the impedance of the conductive layer 1, the first connecting member 19, and the second connecting member 22, the impedance of the first connecting member 19 and the second connecting member 22 is dominant. For example, if the first connecting member 19 and the second connecting member 22 are aluminum foil and have a thickness of 35 μm, a width of 5 mm, and a length of 100 mm, because the resistivity of aluminum is $2.65 \times 10^{-8}$ ($\Omega$m), the impedance of (1) becomes approximately 3 milli-ohms (m$\Omega$). Therefore, by setting the second impedance element 24 and the third impedance element 25 to be greater than or equal to 3 milli-ohms (m$\Omega$), it becomes possible to cause the induced current to efficiently divert to the conductive layer 1, and it is possible to reduce image noise. Here, the second impedance element 24 and the third impedance element 25 may be elements that are not resistors, and at the least may be anything if they are 3 milli-ohms or more in 1 kHz to 100 kHz which is the frequency band of the alternating current magnetic field noise.

In addition, from the perspective of the radiation noise, in the vicinity of the output circuit 13, it is also suitable to provide and add a bypass capacitor of around 100 pF to 0.1 μF between the drive-off bias and the ground of the output board 12. The first impedance element 21 becomes an impedance higher than the added bypass capacitor by the influence of ESL (equivalent series inductance) in the region of an order of MHz to GHz which is where radiation noise becomes a problem. In other words, noise current of the frequency domain where radiation noise is a problem flows, via the bypass capacitor, through the support base 3 or the ground of the output board 12. Regarding the radiation noise, because typically the path becomes smaller the closer the signal source (the drive-off bias in this case) and the return current therefor become, it is possible to effectively reduce the radiation noise by adding a bypass capacitor as described above.

Third Embodiment

Figure 7A:
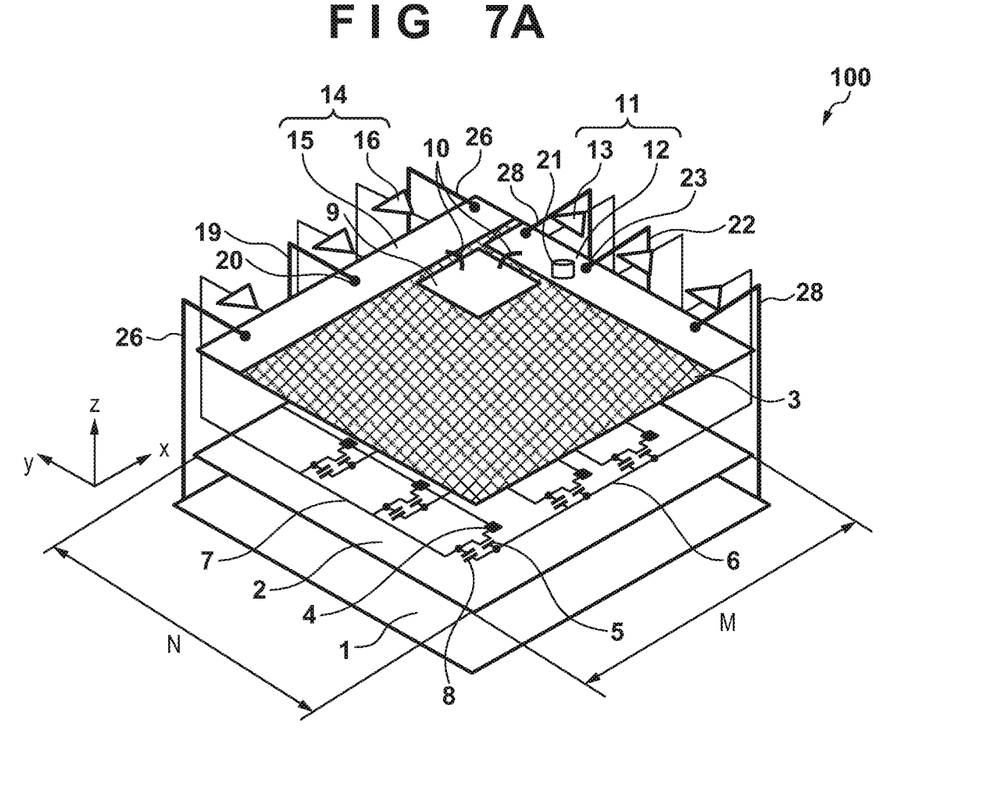
FIGS. 7A and 7B are views that illustrate an example of a structure of a radiation detection apparatus according to a third embodiment.
Figure 7B:
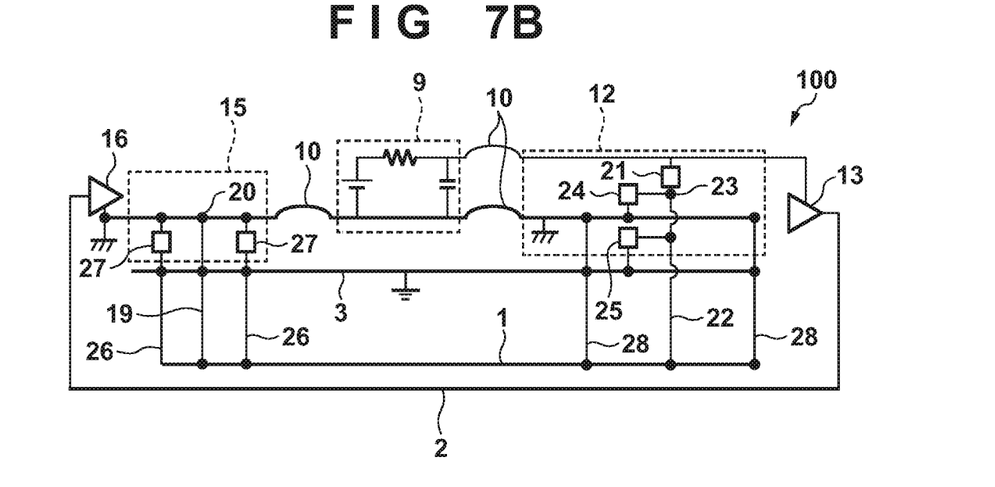

FIGS. 7A and 7B illustrate a structure of the radiation detection apparatus 100 according to a third embodiment. FIG. 7A is the perspective view of the radiation detection apparatus 100 according to the third embodiment. FIG. 7B is the schematic diagram of the circuit of the radiation detection apparatus 100 according to the third embodiment. Note that, in the third embodiment (FIGS. 7A and 7B), the same reference numerals are added for configurations that are the same as the first embodiment (FIG. 1A, FIG. 1B) and the second embodiment (FIG. 6).

The radiation detection apparatus 100 of the third embodiment differs to the first and second embodiments described above in the following points. Specifically, a point in that a plurality of a third connecting member 26 are connected between the conductive layer 1 and the ground of the readout board 15 via a fourth impedance element 27; and a point in that a plurality of a fourth connecting member 28 is connected between the conductive layer 1 and the ground of the output board 12.

In the first embodiment and the second embodiment, it was discussed that it is suitable for the first connecting member 19 and the second connecting member 22 to be connected at an approximate center on respective sides of the sensor array 2. From a perspective other than an alternating current magnetic field, to reduce the influence on image noise due to radiation noise or power supply fluctuation for example, there are cases in which the conductive layer 1 is connected to the output board 12, the ground of the readout board 15, or the support base 3 by a plurality of connection points. In FIGS. 7A and 7B, the third connecting member 26 or the fourth connecting member 28 correspond to these.

However, if the third connecting member 26 is directly connected to the ground of the readout board 15, an induced current due to an alternating current magnetic field that flows or leaks from the conductive layer 1 diverts to the third connecting member 26 and the first connecting member 19. Because of this, the cancelling effect for an induced electromotive force relating to an alternating current magnetic field in the X direction or the area reduction effect relating to an alternating current magnetic field in the Y direction stated in the first embodiment and the second embodiment become smaller. In particular, with respect to a length M of a side of the sensor array 2 at which the readout circuits 16 are connected, if the third connecting member 26 is arranged closer to an end portion than M/4 from either of both ends, the area reduction effect will become even smaller. Accordingly, in the third embodiment, by connecting the conductive layer 1 and the ground of the readout board 15 via the fourth impedance element 27, an induced current that diverts to the third connecting member 26 is made smaller. By this, most of the induced current due to the alternating current magnetic field flows to the first connecting member 19, and it is possible to realize a noise reduction effect similar to that of the first embodiment and the second embodiment described above. Here, it is advantageous for the fourth impedance element 27 to be an impedance of 3 milli-ohms (m$\Omega$) or more for each third connecting member 26, due to the reason stated in the second embodiment.

As described above, the radiation detection apparatus according to each embodiment described above uses a conductive connecting member to changes the path of closed circuits that an external alternating current magnetic field intersects, and reduces image noise by a cancelling effect and an area reduction effect in accordance with a plurality of the closed circuits. Accordingly, exceptional control for noise reduction at a time of capturing becomes unnecessary. In addition, even in a case in which the amplitude or frequency of the alternating current magnetic field is unknown or changes part way through capturing, the cancelling effect and the area reduction effect are not influenced, and stable reduction of image noise is possible. In this way, by virtue of the radiation detection apparatus of each embodiment described above, even in a case in which the frequency or the amplitude of an alternating current magnetic field that arrives from outside is unknown or have changed part way through capturing, it is possible to reduce image noise due to the external alternating current magnetic field without causing a reduction of image capturing operation speed.

<Example of Evaluation Results for Noise Reduction>

To verify the effect of the embodiments described above, evaluation results of an amount of noise are indicated below for a case in which a radiation detection apparatus according to each of the embodiments described above is used in a cassette type X-ray digital image capturing apparatus used for capturing a human body. In the following example of evaluation results, an example of a case in which a 25 kHz sinusoidal current is applied to a one meter square loop coil as an external alternating current magnetic field is indicated.

[Evaluation 1]

In an X-ray digital image capturing apparatus that uses the radiation detection apparatus 100 of the first embodiment, something in which the size of the sensor array 2 is M=approximately 365 mm and N=approximately 440 mm is used. In addition, aluminum having approximately the same shape as the sensor array 2 is used as the conductive layer 1, and the thickness thereof is set to 30 µm. The first connecting member 19 is formed integrated with the conductive layer 1, and its size is length of approximately 60 mm and width of approximately 12 mm. For the first connecting member 19, a metal screw is used to join the readout board 15 to the support base 3, and it connects to two places. If a side of the sensor array 2 to which the output circuits 13 are connected is set as an origin point, the connection positions are respectively set at positions of 140 mm (approximately (1.52/4)×M) and 235 mm (approximately (2.56/4)×M) from the origin point. The second connecting member 22 is formed integrated with the conductive layer 1, and its size is length of approximately 30 mm and width of approximately 12 mm. For the second connecting member 22, a metal screw is used to join and connect the output board 12 to the support base 3. If the side of the sensor array 2 to which the readout circuits 16 are connected is set as the origin point, the connection position is a position 205 mm (approximately (1.86/4)×N) from the origin point. In addition, as the first impedance element 21 that connects the drive-off bias wiring and the ground of the output board 12, a 68 µF capacitor is used and arranged at a position that is separated from the position at which the second connecting member 22 is connected to the support base by approximately 5 mm.

Meanwhile, as the radiation detection apparatus 200 according to FIG. 2A and FIG. 2B which is the comparative example, for the conductive layer 1 something similar to that in the radiation detection apparatus 100 of the first embodiment is used. However, the first connecting member 19 and the second connecting member 22 are not used, and a 68 µF capacitor as the first impedance element is arranged on the power supply board 9.

To what degree a reduction effect was obtained for the image noise amount captured with such a configuration was evaluated after setting the image noise amount in the case of FIG. 2A and FIG. 2B which is the comparative example to 100%. As a result, by using the radiation detection apparatus 100 of the first embodiment, it was possible to reduce image noise due to an alternating current magnetic field from the X direction to 66%, and reduce image noise due to an alternating current magnetic field from the Y direction to 72%. In other words, by the radiation detection apparatus 100 of the first embodiment, it was possible to confirm that an effect of reducing image noise due to an alternating current magnetic field from the X direction and the Y direction by 34% and 28% was obtained.

[Evaluation 2]

In the evaluation 2, an evaluation was performed for an X-ray digital image capturing apparatus in which the radiation detection apparatus 100 of the second embodiment described above was used. In the evaluation 2, plastic screws were used to fix the second connecting member 22 to the support base 3, and the third impedance element 25 was set to an approximately infinite impedance (an open state). In addition, a 0.5Ω resistor was used between the second connection point 23 and the ground of the output board 12 as the second impedance element 24. Other configurations were similar to that in the evaluation 1 described above, and explanation thereof is omitted.

To what degree a reduction effect was obtained for the image noise amount captured with such a configuration was evaluated after setting the image noise amount in the case of FIG. 2A and FIG. 2B which is the comparative example to 100%. As a result, by using the radiation detection apparatus of the second embodiment, it was possible to reduce image noise due to an alternating current magnetic field noise from the X direction to 16%, and reduce image noise due to alternating current magnetic field noise from the Y direction to 59%. In other words, by the radiation detection apparatus of the second embodiment, it was possible to confirm that an effect of reducing image noise due to an alternating current magnetic field from the X direction and the Y direction by 84% and 41% was achieved. Note that a similar evaluation was performed by causing the second impedance element 24 to change from 1Ω to 200Ω, but it was possible to confirm that the reduction effect did not substantially change from the case of 0.5Ω.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2016-052965, filed Mar. 16, 2016, which is hereby incorporated by reference herein in its entirety.

What is claimed is:

1. A radiation detection apparatus, comprising:
a planar radiation detecting panel in which a plurality of detecting units for detecting radiation are arranged in a two-dimensional array by driving signal lines and image signal lines;
an output circuit configured to drive the driving signal lines to cause driving of the detecting units;
a readout circuit configured to read, via the image signal lines, a signal from the detecting units that are driven;
a conductive layer arranged close to the radiation detecting panel;
a first connecting member that connects the ground of the readout circuit and the conductive layer; and
a second connecting member that connects the conductive layer and wiring for providing a drive-off bias to the driving signal lines,
wherein a closed circuit in which an induced current caused by an alternating current magnetic field flows is formed by the first connecting member, the second connecting member, the driving signal line, the image signal line, and the conductive layer, and
the first connecting member is connected to the radiation detecting panel in a position between ¼ and ¾ of a length of a side of the radiation detecting panel to which the readout circuit is connected.

2. The apparatus according to claim 1, wherein the first connecting member is connected to a center of the side of the radiation detecting panel to which the readout circuit is connected.

3. The apparatus according to claim 1, wherein the second connecting member is connected between ¼ and ¾ of a length of a side of the radiation detecting panel to which the output circuit is connected.

4. The apparatus according to claim 3, wherein the second connecting member is connected to a center of the side of the radiation detecting panel to which the output circuit is connected.

5. The apparatus according to claim 1, wherein the second connecting member connects, via a first impedance element, the conductive layer and the wiring for providing the drive-off bias to the output circuit.

6. The apparatus according to claim 5, wherein
the first impedance element is provided in an output board for controlling the output circuit, and connects the wiring for providing the drive-off bias and a ground of the output board, and
the second connecting member connects the conductive layer and a ground of the first impedance element.

7. The apparatus according to claim 5, wherein an impedance of the first impedance element is less than or equal to an impedance of a power supply for supplying the drive-off bias in at least a frequency band of 1 kHz to 100 kHz.

8. The apparatus according to claim 1, wherein
the drive-off bias is a ground potential,
in an output board for controlling the output circuit, wiring for providing the drive-off bias and the ground of the output board are short-circuited, and
the second connecting member connects the conductive layer and a ground of the output board.

9. The apparatus according to claim 1, wherein the second connecting member and a ground of an output board for controlling the output circuit are connected via a second impedance element.

10. The apparatus according to claim 9, wherein an impedance of the second impedance element is 3 milli-ohms or more in at least a frequency band of 1 kHz to 100 kHz.

11. The apparatus according to claim 9,
further comprising a grounded support base that fixes the output board for controlling the output circuit and a readout board for controlling the readout circuit,
wherein the second connecting member and the support base are connected via a third impedance element.

12. The apparatus according to claim 11,
wherein an impedance of the third impedance element is 3 milli-ohms or greater in at least a frequency band of 1 kHz to 100 kHz.

13. The apparatus according to claim 1, further comprising
a plurality of third connecting members, provided separately from the first connecting member, that connect, via a fourth impedance element, the conductive layer and a ground of a readout board for controlling the readout circuit, and
a plurality of fourth connecting members, provided separately from the second connecting members, that connect the conductive layer and a ground of an output board for controlling the output circuit.

14. The apparatus according to claim 13, wherein an impedance of the fourth impedance element is 3 milli-ohms or more in at least a frequency band of 1 kHz to 100 kHz.

15. The apparatus according to claim 1, wherein the conductive layer is a thin film that covers the radiation detecting panel.

16. The apparatus according to claim 1, wherein the conductive layer is a sheet type conductive material.

17. A radiation detection apparatus, comprising:
a planar radiation detecting panel in which a plurality of detecting units for detecting radiation are arranged in a two-dimensional array by driving signal lines and image signal lines;
an output circuit configured to drive the driving signal lines to cause driving of the detecting units;
a readout circuit configured to read, via the image signal lines, a signal from the detecting units that are driven;
a conductive layer arranged close to the radiation detecting panel;
a first connecting member that connects the ground of the readout circuit and the conductive layer; and a second connecting member that connects the conductive layer and wiring for providing a drive-off bias to the driving signal lines, wherein a closed circuit in which an induced current caused by an alternating current magnetic field flows is formed by the first connecting member, the second connecting member, the driving signal line, the image signal line, and the conductive layer, and the second connecting member is connected to the radiation detecting panel in a position between ¼ and ¾ of a length of a side of the radiation detecting panel to which the output circuit is connected.

18. A radiation imaging system, comprising:

an emitting unit configured to emit radiation;

a radiation detection apparatus; and a formation unit configured to irradiate radiation by the emitting unit and form a radiation captured image based on a signal read by the readout circuit of the radiation detection apparatus, wherein the radiation detection apparatus comprises a planar radiation detecting panel in which a plurality of detecting units for detecting radiation are arranged in a two-dimensional array by driving signal lines and image signal lines, an output circuit configured to drive the driving signal lines to cause driving of the detecting units, a readout circuit configured to read, via the image signal lines, a signal from the detecting units that are driven, a conductive layer arranged close to the radiation detecting panel, a first connecting member that connects the ground of the readout circuit and the conductive layer, and a second connecting member that connects the conductive layer and wiring for providing a drive-off bias to the driving signal lines, wherein a closed circuit in which an induced current caused by an alternating current magnetic field flows is formed by the first connecting member, the second connecting member, the driving signal line, the image signal line, and the conductive layer, and the first connecting member is connected to the radiation detecting panel in a position between ¼ and ¾ of a length of a side of the radiation detecting panel to which the readout circuit is connected.

\* \* \* \* \*